United States Patent [19]

Holland et al.

[11] 4,056,574

[45] Nov. 1, 1977

[54] OXIDATIVE COUPLING PROCESS

[75] Inventors: David Holland; David John Milner, both of Runcorn; Hugh Wilma Boulton Reed, Middlesborough, all of England

[73] Assignee: Imperial Chemical Industries Limited, London, England

[21] Appl. No.: 680,124

[22] Filed: Apr. 26, 1976

[30] Foreign Application Priority Data

Apr. 28, 1975 United Kingdom ............... 17511/75

[51] Int. Cl.$^2$ ............................................. C07C 21/00
[52] U.S. Cl. ................................................ 260/654 R
[58] Field of Search ............................ 260/654 R, 653

[56] References Cited

U.S. PATENT DOCUMENTS 3,730,957  5/1973  Bozik et al. ...................... 260/654 R Primary Examiner—C. Davis
Attorney, Agent, or Firm—Cushman, Darby & Cushman

[57] ABSTRACT

Isobutene is oxidatively coupled with vinylidene chloride by heating in the presence of palladium acetate, to give 1,1-dichloro-4-methylpenta-1,3-diene. This compound is useful as an intermediate in the production of insecticides. Any 1,1-dichloro-4-methylpenta-1,4-diene also produced is thermally isomerized to the 1,3 product.

6 Claims, No Drawings

OXIDATIVE COUPLING PROCESS

This invention relates to the preparation of chemical intermediates useful in the preparation of insecticides and especially to the preparation of 1,1-dichloro-4-methylpenta-1,3-diene by oxidatively coupling isobutene with vinylidene choride.

It is known that certain substituted α-olefins (e.g. isobutene) yield substituted butadienes when treated with palladium (II) in acetic acid at 80° C (H. C. Volger, Rec Trav. Chim., 86, 677, 1967). It is also know that under similar conditions vinyl chloride is converted to vinyl acetate (C. F. Kohll, Rec. Trav Chim., 87, 481, 1968). Furthermore, treatment of vinylidene chloride in the same way results in reduction of the palladium acetate to palladium metal with no production of dimeric products.

It is thus most surprising that when a mixture of isobutene and vinylidene chloride is treated with palladium acetate, chlorinated dienes are produced.

According to the present invention a process for the preparation of 1,1-dichloro-4-methyl penta-1,3-diene of formula

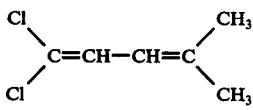

comprises oxidatively coupling isobutene with vinylidene chloride in the presence of palladium acetate.

The reaction is carried out homogeneously in the liquid phase, preferably using the vinylidene chloride as the liquid medium. However, solvents may be used if desired. Suitable solvents, which must be polar organic liquids resistant to oxidation under the prevailing conditions, include dimethyl formamide, dimethylacetamide and nitrobenzene.

The palladium acetate may either be added to the reaction mixture as such or may be formed in situ by adding palladium metal and acetic acid, but when this is done it is necessary to add nitric acid to oxidise the Pd(O) to Pd(II).

In order to prepare palladium (II) acetate, it is normally necessary to either react palladium metal with acetic acid and nitric acid, or to treat palladium nitrate with acetic acid. In either case, nitrogenous compounds are present in the palladium acetate produced, and we have found that their presence improves the selectivity of our process with respect to the desired reaction products. For example, if the nitrogen content of the palladium acetate is reduced, e.g. by recrystallisation, the selectivity also reduced. In general, we find that the palladium acetate preferably has a nitrogen content (determined as described below) in the range of 0.1 to 3.0% by weight.

In this context, the "nitrogen content" of the palladium acetate may be determined by any of the known methods of elemental analysis for organic compounds. For example, a sample of the palladium acetate may be combusted at 1100° C and the combustion products analysed by gas/liquid chromatography.

The concentration of palladium acetate in the reaction mixture is not critical; but since the reaction is a homogeneous one, the upper limit of concentration is determined by the solubility of the palladium acetate in the reactants and/or solvent, when present. In general, concentrations of palladium acetate do not exceed 5 mole %.

The oxidative coupling reaction proceeds at moderate temperatures, for example in the range 50° to 150° C, temperatures in the range 50°-70° C being particularly suitable. Ambient pressure is conveniently used, but the use of elevated pressure is not precluded, and reactions are often conducted in an autoclave under autogenous pressure. The reaction may be conducted in the presence of oxygen or under an inert gas such as nitrogen.

As the reaction proceeds the palladium (II) is reduced to palladium (O) metal, which may be subsequently removed from the reacted mixture, e.g. by filtration, and re-used. Alternatively, especially when the reaction is conducted in the presence of oxygen, conditions may be arranged so that the palladium (II) is regenerated in situ, the reaction products being removed continuously from the reaction vessel, e.g, by distillation. It may be desirable to incorporate another variable valency metal, e.g. copper or iron in the reaction system to facilitate regeneration of the palladium (II).

The reaction product comprises a mixture of 1,1-dichloro-4-methylpenta-1,3-diene, 1,1-dichloro-4-methyl penta 1,4-diene, 2,5 dimethylhexa-2.4-diene and 2,5 dimethylhexa-b 1,3-diene with minor amouts of other dimers of isobutene. However, the relative proportions of the components of the mixture depends on the nitrogen content of the palladium acetate, as discussed above. The ratio of vinylidene chloride to isobutene in the reaction mixture also has an effect on the course of the reaction. For example, at low levels of vinylidene chloride (VDC: isobutene ratios <0.5 to 1) mainly dehydrodimers of isobutene are produced, whereas at very high levels of vinylidene chloride (VDC:isobutene ratios of 30 to 1 and above) mainly chloro-acetate products result. It is thus preferred that the VDC:isobutene ratio is in the range 0.5 to 1 to 25 to 1. Furthermore, when working in the afore-mentioned range, ratios from 2 to 1 to 15 to 1 are especially preferred, since when working within this restricted range, the yields of dehydrodimers, especially with respect to the desired products, are greatest, calculated on the amount of palladium acetate reduced.

The 1,1-dichloro-4-methylpenta-1,4-diene may be readily isomerised to the desired 1,1-dichloro-4 methylpenta-1,3-diene by heating, for example at a temperature in the range 80°-150° C in the presence of a catalytic amoount of p-toluene sulphonic acid. The desired product may be separated from the reaction mixture by suitable means, for example by fractional distillation.

1,1-dichloro-4-methylpenta-1,3-diene may be used in the preparation of compounds which are useful as insecticides.

Derivatives of 2,2-dimethyl-3-(2,2-dichlorovinyl) cyclopropane carboxylic acid, particularly the 5benzyl-3-furyl-methyl and the 3-phenoxybenzyl esters have recently been proposed as insecticides. They may be prepared by converting 2,2-dimethyl-3-(2,2-dichlorovinyl) cyclopropane carboxylic acid to its acid chloride and reacting the acid chloride with either 5-benzyl-furylmethanol or 3-phenoxybenzyl alcohol. The 2,2-dimethyl-3-(2,2-dichlorovinyl) cyclopropane carboxylic acid is obtained by hydrolysis of a lower alkyl ester (for example the methyl or ethyl ester) which may be prepared by the method of Farkas et al. (Collection Czechoslovak Chem. Commun. 1959, 24, 2230-6) from 1,1-dichloro-4- methyl-1,3-pentadiene and the lower alkyl ester of diazoacetic acid.

The invention will now be illustrated by the following Examples.

EXAMPLE 1

Palladium acetate (2 m moles) was added, under an atmosphere of nitrogen, to vinylidene chloride (400 m mole) contained in a glass-lined autoclave. The mixture was stirred at ambient temperature to give a deep red-brown solution of palladium acetate in vinyldiene chloride. Isobutene (160 m mole) was added to this solution and the autoclave was sealed. (Ratio of VDC:isobutene = 2.5 to 1). The reaction mixture was then heated to 60° C with continual stirring and maintained at this temperature for 30 minutes. After cooling to ambient temperature excess isobutene was vented from the autoclave and the reaction mixture filtered to remove the black precipitate of palladium metal. The precipitate was washed with hexane and dried to constant weight; it was found to be equivalent to 0.5 mg atoms of palladium. The palladium acetate used in this Example, and Examples 2 and 3, had a nitrogen content of 0.57% by weight.

The product solution was then analysed using a Perkin-Elmer F11 gas liquid chromatograph (g.l.c) using a 2 m $\beta\beta'$oxydipropionitrile column maintained at 70° C, linked to a mass spectrograph.

The principal products proved to be as follows:

i. 1,1-dichloro-4-methylpenta-1,3-diene — (0.11 m mole)
ii. 1,1-dichloro-4-methylpenta-1,4-diene — (0.06 m mole)
iii. Other non-chlorinated diens — (0.33 m mole)

Since product (ii) was readily isomerised to product (i) as described above, it will be seen that the yield of the desired product was 34% based on the amount of palladium reduced to metal, while the total yield was 100%.

EXAMPLE 2

Palladium acetate (2 m mole) was dissolved in dimethyl formamide (20 ml). Vinylidene chloride (50 m mole) was added and to the palladium acetate solution and the mixture placed in a glass-lined autoclave. After flushing with nitrogen and venting, liquid isobutene (70 m mole) was added and the autoclave sealed. (Ratio of VDC: isobutene = 0.7 to 1). The temperature of the stirred reaction mixture was raised to 60° C and maintained at this temperature for 120 minutes. After cooling the reduced palladium was separated and weighed (1.1 mg atoms) and the products analysed as described in Example 1. The products were as follows:

1,1-dichloro-4-methylpenta-1,3-diene — 0.025 m mole
1,1-dichloro-4-methylpenta-1,4-diene — 0.05 m mole
Other non-chlorinated dienes — 0.86 m mole It will be seen that with a VDC:isobutene ratio of 1.5 to 1, the yield of desired products was 6.8% and total yield 85%.

EXAMPLE 3

Palladium acetate (2.0 m mole) and ferric acetonylacetate (5.0 m mole) was added to vinylidene chloride (370 m mole). The clear solution which was obtained on stirring was placed in a glass-lined autoclave. After flushing with nitrogen and venting, liquid isobutene (107 m mole) was added and the autoclave sealed. The temperature of the stirred reaction mixture was raised to 60° C and maintained at this temperature for 17 hours. After cooling, the reduced palladium was separated and weighed and the products analysed as described in Example 1. The products were as follows:

1,1-dichloro-4-methylpenta-1,3-diene — 0.05 m mole
1,1-dichloro-4-methylpenta-1,4-diene — 0.03 m mole
Other non-chlorinated dienes — 0.77 m mole The weight of precipitated Pd was 0.5 m atom.

Hence, as the total products amounted to 0.85 m mole there was a 170% total yield based on palladium reduced, demonstrating that some regeneration of Pd(II) had taken place.

EXAMPLE 4

Palladium acetate (2 m mole, nitrogen content 0.04%) was dissolved in dimethyl formamide (20 ml). Vinylidene chloride (50 m mole) was added to the palladium acetate solution and the mixture placed in a glass-lined autoclave. After flushing with nitrogen and venting, liquid isobutene (70 m mole) was added and the autoclave sealed. The temperature of the stirred reaction mixture was raised to 60° C and maintained at that temperature for 120 minutes. After cooling, the reduced palladium metal was separated and weighed and the products analysed as described in Example 1. The products were as follows:

1,1-dichloro-4-methylpenta-1,3-diene — 0.005 m mole
Other non-chlorinated dienes — 1.11 m mole This Example demonstrates the reduction of selectivity with respect to the desired chlorinated diene, when the nitrogen content of the palladium acetate was reduced.

What we claim is:

1. A process for the preparation of 1,1-dichloro-4-methyl penta-1,3-diene of formula

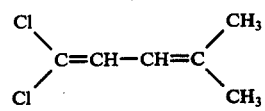

which comprises oxidatively coupling isobutene with vinylidene chloride by heating them together in homogeneous liquid medium in the presence of a catalytic amount of palladium acetate at a temperature in the range 50° to 150° C, the ratio of isobutene to vinylidene chloride being in the range 2 to 1 to 15 to 1.

2. A process according to claim 1 in which the nitrogen content of the palladium acetate is in the range 0.1 to 3% by weight.

3. A process according to claim 1 which is conducted at a temperature in the range 50° to 70° C.

4. A process according to claim 1 in which any 1,1-dichloro-4-methyl penta-1,4-diene produced is thermally isomerised to 1,1-dichloro-4-methyl penta-1,3-diene by heating it to a temperature in the range 80° to 150° C in the presence of a catalyst.

5. A process according to claim 4 wherein the catalyst is p-toluene sulphonic acid.

6. A process according to claim 1 wherein the palladium acetate concentration does not exceed 5 mole %.

UNITED STATES PATENT AND TRADEMARK OFFICE
CERTIFICATE OF CORRECTION

PATENT NO. : 4,056,574

DATED : November 1, 1977

INVENTOR(S) : DAVID HOLLAND, DAVID JOHN MILNER AND HUGH WILMA BOULTON

It is certified that error appears in the above-identified patent and that said Letters Patent are hereby corrected as shown below:

Please amend claim 1 as follows:

Column 4, lines 52-53 delete "the ratio of isobutene to vinylidene chloride" and insert --the ratio of vinylidene chloride to isobutene--.

Signed and Sealed this

Seventeenth Day of April 1979

[SEAL]

Attest:

RUTH C. MASON
Attesting Officer

DONALD W. BANNER
Commissioner of Patents and Trademarks